United States Patent
Ciambecchini et al.

(10) Patent No.: US 9,272,982 B2
(45) Date of Patent: Mar. 1, 2016

(54) METHOD FOR PREPARING HIGH-PURITY FESOTERODINE FUMARATE

(71) Applicant: CHEMI S.P.A., Cinisello Balsamo (IT)

(72) Inventors: Umberto Ciambecchini, Patrica (IT); Elio Ullucci, Patrica (IT); Stefano Turchetta, Patrica (IT); Maurizio Zenoni, Patrica (IT)

(73) Assignee: CHEMI S.P.A., Cinisello Balsamo (IT)

(*) Notice: Subject to any disclaimer, the term of this patent is extended or adjusted under 35 U.S.C. 154(b) by 0 days.

(21) Appl. No.: 14/308,828

(22) Filed: Jun. 19, 2014

(65) Prior Publication Data

US 2014/0303396 A1 Oct. 9, 2014

Related U.S. Application Data

(63) Continuation of application No. 12/779,216, filed on May 13, 2010, now abandoned.

(30) Foreign Application Priority Data

May 15, 2009 (IT) .............................. MI2009A0845

(51) Int. Cl.
  *C07C 227/16* (2006.01)
  *C07C 59/40* (2006.01)
  *C07C 219/28* (2006.01)

(52) U.S. Cl.
  CPC ............... *C07C 227/16* (2013.01); *C07C 59/40* (2013.01); *C07C 219/28* (2013.01)

(58) Field of Classification Search
  CPC ...... C07C 227/16; C07C 59/40; C07C 219/28
  See application file for complete search history.

(56) References Cited

U.S. PATENT DOCUMENTS

| 6,858,650 B1 | 2/2005 | Meese |
| 8,049,031 B2 | 11/2011 | Ciambecchini et al. |
| 2010/0292503 A1 | 11/2010 | Ciambecchini et al. |
| 2011/0086103 A1 | 4/2011 | Charugundla et al. |
| 2012/0220655 A1* | 8/2012 | Kerekes ........................ 514/546 |

FOREIGN PATENT DOCUMENTS

| WO | 2007/140986 | 12/2007 |
| WO | 2009/037569 | 3/2009 |
| WO | 2009/044278 | 4/2009 |
| WO | WO 2009/044278 | * 4/2009 |
| WO | WO 2010/018484 | * 2/2010 |

OTHER PUBLICATIONS

Search Report for Italian Application No. MI2009A000845, dated Jan. 26, 2010.
Mroweitz et al. Brit. J. Dermatol. 1999, 141, 424-429.
Litjens et al., BMC Pharmacology 2004, 4:22.
Kappos et al., Lancet 2008, 372, 1463-1472.

\* cited by examiner

*Primary Examiner* — Nyeemah A Grazier
*Assistant Examiner* — Amanda L Aguirre
(74) *Attorney, Agent, or Firm* — Silvia Salvadori, P.C.; Silvia Salvadori

(57) ABSTRACT

A process is described for preparing fesoterodine fumarate comprising the salification reaction of fesoterodine with fumaric acid in an organic solvent, preferably a ketone, at a temperature not greater than 45° C. Such process allows obtaining products with high yields and purities, and in particular a product having a content of (2E)-4-[(3-(3-diisopropylamino-1-phenylpropyl)-4-(2-isobutyroyloxyphenyl) methoxy]-4-oxobut-2-enoic acid less than or equal to 0.15% by mole.

17 Claims, No Drawings

METHOD FOR PREPARING HIGH-PURITY FESOTERODINE FUMARATE

CROSS-REFERENCE TO RELATED APPLICATIONS

This application is a continuation of U.S. application Ser. No. 12/779,216 filed on May 13, 2010 which claims priority to and benefit of Italian Application No. MI2009A000845 filed on May 15, 2009, the contents of which are incorporated herein by reference in their entireties.

FIELD OF THE INVENTION

The object of the present invention is a process for preparing fesoterodine fumarate comprising the salification reaction of fesoterodine with fumaric acid in an organic solvent, preferably a ketone, at a temperature not greater than 45° C.

BACKGROUND OF THE INVENTION

Fesoterodine fumarate is the international nonproprietary name (INN) of the active principle 2-((R)-3-diisopropylammonium-1-phenylpropyl)-4-(hydroxymethyl) phenyl isobutyrate hydrogen fumarate, whose structure formula is reported hereinbelow.

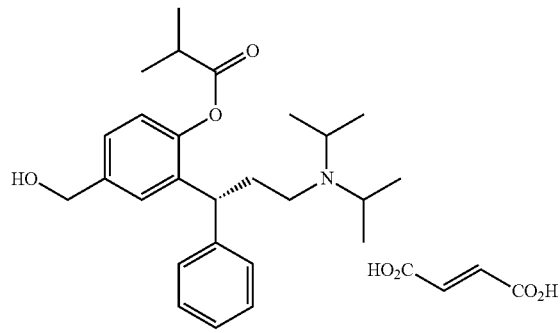

Fesoterodine fumarate was approved in Europe and in the U.S.A. for the treatment of overactive bladder syndrome with the commercial name of TOVIAZ®.

Fesoterodine fumarate was described for the first time in U.S. Pat. No. 6,858,650, which reports the preparation of the active ingredient by the salification of fesoterodine with fumaric acid, according to scheme 1 reported below.

Scheme 1

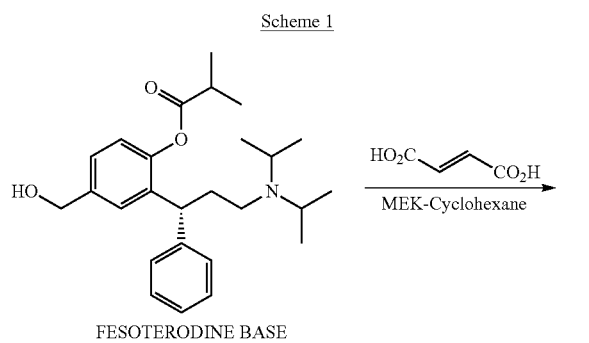

FESOTERODINE BASE

FESOTERODINE FUMARATE

In turn, fesoterodine (also called fesoterodine base) is described in U.S. Pat. No. 6,713,464, where it is prepared starting from a deacylated precursor, (R)-feso deacyl, i.e. (R)-2-[3-(diisopropylamino)-1-phenylpropyl]-4-(hydroxymethyl)phenol, according to scheme 2 reported hereinbelow.

Scheme 2

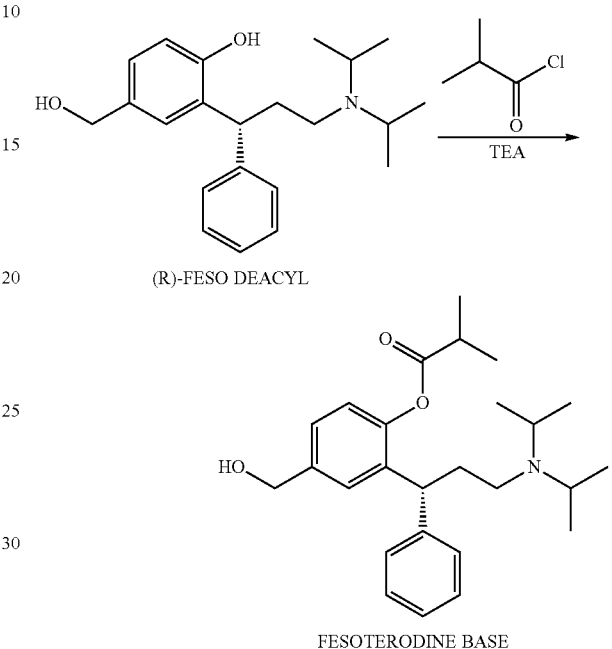

(R)-FESO DEACYL

FESOTERODINE BASE

The preparation of (R)-feso deacyl is instead described in U.S. Pat. No. 5,559,7269.

DETAILED DESCRIPTION OF THE INVENTION

During the salification experiments of fesoterodine with fumaric acid, it was found that in the salification reaction, variable quantities of a by-product can be formed that is not reported in the literature. Such by-product was identified as a fesoterodine monofumarate, i.e. (2E)-4-[(3-(3-diisopropylamino-1-phenylpropyl)-4-(2-isobutyroyloxyphenyl)methoxy]-4-oxobut-2-enoic acid, whose structure formula is reported hereinbelow.

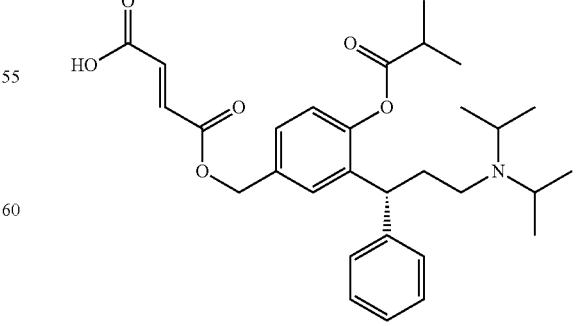

FESO FUMARIC ESTER IMPURITY

Such impurity, named "feso fumaric ester" impurity for convenience, can increase up to values greater than 1% if the salification conditions are not suitable controlled.

The feso fumaric ester impurity has been synthesized and characterized, and salification conditions of fesoterodine with fumaric acid have been identified (constituting the object of the present invention) such that the quantity of feso fumaric ester impurity in the finished product is maintained below the ICH limits allowed for known impurities (≤0.15% by mole).

Both the process for the preparation of fesoterodine fumarate via salification of fesoterodine with fumaric acid and the fesoterodine fumarate thus obtained constitute the object of the present invention; and in particular, a fesoterodine fumarate having a content of feso fumaric ester impurity below 0.15% by mole.

The process according to the present invention comprises the salification reaction of fesoterodine with fumaric acid in at least one suitable organic solvent at a temperature not higher than 45° C., preferably at a temperature comprised between 30 and 40° C., still more preferably at about 35° C.

In practice, such salification reaction is carried out by heating a mixture of fesoterodine and fumaric acid at the aforesaid temperature in the aforesaid at least one organic solvent, until complete dissolution; such operation normally requires from 10 minutes to two hours, preferably from 30 minutes to one hour. The solution thus obtained is then cooled at a temperature lower than 25° C., preferably comprised between 5 and 20° C., still more preferably between 15 and 20° C.

The precipitation of the salt can be triggered with methods known in the art, for example via addition of a crystalline fesoterodine fumarate seed or by means of addition of solid fesoterodine fumarate obtained via lyophilization of an aqueous solution of fesoterodine fumarate.

The fesoterodine usable in the process of the present invention can be obtained according to one of the methods reported in the literature, for example according to the method reported in U.S. Pat. No. 6,713,464, incorporated herein by reference; it can also be used either in pure or crude form.

According to one aspect of the invention, the organic solvent is preferably a polar aprotic organic solvent, preferably a ketone, still more preferably a ketone having from three to six carbon atoms; according to the more preferred embodiment, such ketone is methylethylketone (i.e. 2-butanone).

According to a further aspect of the invention, fumaric acid is used in molar ratios comprised between 0.9 and 1.5 (preferably between 1.0 and 1.1) with respect to fesoterodine; fesoterodine, in turn, is used in a weight/volume ratio (g/l) comprised between 2 and 50, preferably between 3 and 10, with respect to said at least one organic solvent.

Fesoterodine fumarate thus obtained can then be isolated with conventional methods; it is preferably filtered, washed (generally with the same solvent used in the salification reaction) and then dried under vacuum.

The product thus obtained is therefore preferably micronized by using conventional techniques, until a PSD is obtained with d (0.9)≤20 microns, i.e. a Particle Size Distribution in which 90% of the particles have a size that does not exceed 20 microns.

In the following tables, the results of two stability tests are reported that were conducted on samples of fesoterodine fumarate obtained by following the teachings of example 1.

In detail, the experiment related to Table 1 consists of dissolving fesoterodine fumarate in methylethylketone at 40° C., drawing samples of the freshly dissolved solution (time 0), after 1, 3 and 20 hours of maintenance at 40° C. and analyzing them in HPLC in order to verify their purity.

TABLE 1

Solution stability in methylethylketone at T = 40° C.

| | HPLC Purity Area % | (R)-feso-deacyl | Impurity RRt = 1.05 | Impurity RRt = 1.34 | Feso fumaric ester impurity | Diester impurity | RRt = 1.86 |
|---|---|---|---|---|---|---|---|
| t = 0 | 99.87 | n.d. | n.d. | 0.06 | 0.07 | — | — |
| t = 1 hour | 99.85 | n.d. | n.d. | 0.06 | 0.09 | — | — |
| t = 3 hours | 99.77 | 0.01 | n.d. | 0.06 | 0.12 | 0.04 | — |
| t = 20 hours | 99.70 | 0.02 | n.d. | 0.08 | 0.14 | 0.06 | n.d. |

RRt = Relative Retention time (HPLC)
n.d. = not detectable

From the conducted test, it was observed that the feso fumaric ester impurity increases over time until it stabilizes at about 0.14% by mole, i.e. below the specification limit, after 20 hours.

In confirmation thereof, another stability test was carried out at 60° C. on the crystallized solid product, whose results are reported in Table 2. In detail, the experiment consists of introducing a sample of fesoterodine fumarate in an oven capable of maintaining a temperature of 60° C. and 60% relative humidity, drawing samples of the freshly introduced substance (time 0) after 24, 48, 72 and 144 hours staying in such conditions, and analyzing them in HPLC in order to verify their purity.

TABLE 2

Solid stability at T = 60° C. in atmosphere with 60% relative humidity

| | HPLC Purity Area % | (R)-feso-deacyl | Impurity RRt = 1.05 | Impurity RRt = 1.34 | Feso fumaric ester impurity | Diester impurity | RRt = 1.86 |
|---|---|---|---|---|---|---|---|
| t = 0 | 99.85 | 0.02 | n.d. | n.d. | 0.09 | 0.04 | n.d. |
| t = 24 h | 99.83 | 0.02 | n.d. | n.d. | 0.11 | 0.04 | n.d. |
| t = 48 h | 99.74 | 0.02 | n.d. | 0.08 | 0.12 | 0.04 | n.d. |

TABLE 2-continued

Solid stability at T = 60° C. in atmosphere with 60% relative humidity

| | HPLC Purity Area % | (R)-feso-deacyl | Impurity RRt = 1.05 | Impurity RRt = 1.34 | Feso fumaric ester impurity | Diester impurity | RRt = 1.86 |
|---|---|---|---|---|---|---|---|
| t = 72 h | 99.72 | 0.03 | 0.02 | 0.06 | 0.13 | 0.04 | n.d. |
| t = 144 h | 99.64 | 0.05 | 0.03 | 0.07 | 0.14 | 0.04 | 0.03 |

RRt = Relative Retention time (HPLC)
n.d. = not detectable

Also from this stability test, it is confirmed that crystalline fesoterodine fumarate maintained at 60° C. loses purity over time via formation of the feso fumaric ester impurity, which stabilizes after 144 hours (6 days) at around 0.14% by mole.

The following examples clarify in detail the conditions used for obtaining high-purity fesoterodine fumarate according to the present invention; such examples are intended as non-limiting and exemplifying of the present invention.

Example 1

Preparation of fesoterodine fumarate

In a 2-liter reactor, 31.2 g of sodium bicarbonate and 1250 ml of deionized water (pH 8.1) are charged. Stirring is performed until complete dissolution of the salt. In a 10-liter reactor, 250 g of (R)-Feso deacyl and 7500 ml of dichloromethane are charged. Stirring is performed until a complete solution is obtained. Then, the aqueous bicarbonate solution is added to the organic solution and the biphasic mixture is cooled at 5° C. 86 g of isobutyryl chloride are then added dropwise to the mixture, which is once again stirred for one hour from the end of the addition. Then, 1250 ml of a solution of 5% w/w sodium bicarbonate in water are added to the reaction mixture and the mixture is heated at 20° C., still under stirring. The lower organic phase is separated and is first washed with 2500 ml of a solution of 5% w/w sodium bicarbonate in water then twice with 2×2500 ml of deionized water. The obtained organic phase is concentrated to a small volume and 1000 ml of 2-butanone are added thereto. The mixture is once again evaporated to half the initial volume, then 1000 ml of 2-butanone are added again and 80.4 g fumaric acid are added to the solution. The suspension is heated at 35° C. until complete dissolution is obtained. It is cooled at 20° C.; the crystallization is triggered with crystalline fesoterodine fumarate seeds. Stirring is maintained for 1 hour at 20° C. and for 2 hours at 0° C. The suspension is then filtered over a Buchner funnel and the pad is washed with 600 ml of 2-butanone. 621 g of moist product are obtained, which are dried at t=35° C. for 15 hours, obtaining 331 g of crystalline fesoterodine fumarate (85.7% yield). The purity of the product is 99.8%, with (R)-feso deacyl not detectable, diester impurity 0.10% and feso fumaric ester impurity 0.07%.

Example 2

Preparation of fesoterodine fumarate

In a 250 milliliter flask, 3.0 g of (R)-Feso deacyl and 60 ml of dichloromethane are charged. Stirring is performed until a complete solution is obtained. The temperature of the solution is brought to 0-5° C. 1.02 g of isobutyryl chloride dissolved in 30 ml of dichloromethane are added dropwise on the mixture and the mixture is again stirred for ten minutes from the end of the addition. Then, 15 ml of a solution of 2.5% w/w sodium bicarbonate in water (pH 8.1) are added to the reaction mixture and the mixture is stirred at 0-5° C. for another 2 hours. It is then left to warm at room temperature and the lower organic phase is separated, washing it first with 30 ml of a solution of 5% w/w sodium bicarbonate in water and then twice with 2×50 ml of deionized water. The obtained organic phase is concentrated to small volume and 30 ml of 2-butanone are added thereto. The mixture is once again evaporated to half the initial volume, then another 30 ml of 2-butanone are added, and 0.9 g of fumaric acid are added to the solution. The suspension is heated at 35° C. until complete dissolution is obtained. It is cooled at 20° C.; the crystallization is triggered with seeds of crystalline fesoterodine fumarate. Stirring is maintained for 1 hour at 20° C. and for 2 hours at 0° C. Then, the suspension is filtered over a Buchner filter and the pad is washed with 10 ml of 2-butanone. 3.41 g of moist product are obtained, which are dried at t=35° C. for 15 hours, obtaining 3.13 g of crystalline fesoterodine fumarate (85.7% yield). The purity of the product is 99.8%, with (R)-feso deacyl 0.12%, diester impurity 0.07% and feso fumaric ester impurity 0.02%.

The fesoterodine thus obtained can be recrystallized by dissolving it in 21 ml of methylethylketone, bringing the mixture to 40° C. (with dissolution of the suspended material), cooling the solution at 20° C., and seeding the solution with 2 mg of crystalline fesoterodine fumarate. After further cooling at 0-5° C. and keeping in such conditions for two hours, the obtained solid is filtered and washed with methylethylketone, obtaining 3.03 g of moist fesoterodine fumarate, which is dried at 35° C. for 15 hours, obtaining 2.75 g of fesoterodine fumarate (89% yield), having HPLC purity equal to 99.9%, containing (R)-feso deacyl 0.09%, non-detectable diester impurity and feso fumaric ester impurity 0.03%.

Example 3

Preparation of Micronized fesoterodine fumarate 30 g of fesoterodine fumarate prepared according to example 1 are inserted into a Mc One® Fluid Jet Mill micronization apparatus at a nitrogen pressure of the micronization chamber of 4 atmospheres and at a nitrogen pressure of the Venturi tube of 6 atmospheres. The recovered product is subjected to Particle Size Distribution analysis by using a Malvern Mastersizer 2000 Ver. 5.22, Tegiloxan 3 instrument as dispersing agent and a dispersing speed in the instrument of 3000 rpm. The d(0.9) of the product is equal to 24 microns. The product is analyzed for HPLC purity and has identical purity to the starting product (99.8%, with (R)-feso deacyl not detectable, diester impurity 0.10% and feso fumaric ester impurity 0.07%.). The obtained product is also analyzed by means of X ray diffraction of powders and the analysis confirms that the micronized material has the same crystalline form as the starting material.

A second 30 g aliquot of the product prepared according to the example 1 is micronized in the same above-described apparatus, at a nitrogen pressure of the micronization chamber of 6 atmospheres and at a nitrogen pressure of the Venturi tube of 8 atmospheres. The recovered product is subjected to Particle Size Distribution analysis by using a Malvern 2000 instrument. The d(0.9) of the product is equal to 15 microns and the purity of the product remains unchanged with respect to the material inserted in the micronizer. The obtained product is also analyzed by means of X ray diffraction of powders and the analysis confirms that the micronized material has the same crystalline form as the starting material.

Example 4

Preparation of fesoterodine fumaric ester Impurity 5 g of fesoterodine fumarate prepared as in example 1 are dissolved in 150 ml of methylethylketone and the mixture is heated under reflux for a week. At the end, the HPLC analysis detects shows a content of feso fumaric ester impurity of 15%. The solvent is evaporated and the residue is chromatographed on silica gel column, eluting with a mobile phase constituted by 80% dichloromethane and 20% methanol. The column fractions containing the desired impurity are collected and by drying the pooled fractions, 600 mg of the desired impurity are obtained. The spectroscopic data reported below, related to the isolated impurity, confirm the identity of the obtained product.

$^1$H-NMR: δ (DMSOd$^6$): 6.60-7.45 (m, 10H); 5.15 (d, 2H); 4.01 (m, 1H); 3.59-3.52 (m, 4H); 2.87-2.71 (m, 5H); 1.35-1.24 (m, 18H).

$^{13}$C-NMR: δ (DMSOd$^6$): 175.86, 169.55, 166.25, 148.68, 142.19, 141.28, 135.42, 134.79, 129.05, 128.99, 128.08, 127.87, 127.69, 127.17, 123.05, 65.86, 54.54, 46.17, 41.74, 34.37, 31.91, 19.38, 19.23, 18.04, 17.83.

MS (positive ionization): (M+1) 510.54 (100%), 511.40 (36%), 512.35 (7%). Calculated for $C_{30}H_{39}NO_6$: 510.29 (100), 511.29 (36%), 510.29 (7%).

We claim:

1. Method for preparing fesoterodine fumarate having a content of (2E)-4-[(3-(3-diisopropylamino-1-phenylpropyl)-4-(2-isobutyroyloxyphenyl)methoxy]-4-oxobut-2-enoic acid less than or equal to 0.15% by mole, said method comprising:
   reacting fesoterodine with fumaric acid in at least one organic solvent, wherein said reacting step is carried out at a temperature not higher than 45° C.,
   thereby obtaining fesoterodine fumarate having a content of (2E)-4-[(3-(3-diisopropylamino-1-phenylpropyl)-4-(2-isobutyroyloxyphenyl)methoxy]-4-oxobut-2-enoic acid less than or equal to 0.15% by mole,
   wherein said fesoterodine is used in a g/l weight/volume ratio comprised between 2:1 and 50:1 with respect to said at least one organic solvent.

2. The method according to claim 1, wherein said temperature is comprised between 30 and 40° C.

3. The method according to claim 1, further comprising heating a mixture of fesoterodine and fumaric acid in said at least one organic solvent until complete dissolution, and cooling the solution thus obtained at a temperature lower than 25° C.

4. The method according to claim 3, wherein said heating step is carried out for a period comprised between 10 minutes and two hours.

5. The method according to claim 4, wherein said heating step is carried out for a period comprised between 30 minutes and one hour.

6. The method according to claim 3, wherein said cooling step is carried out at a temperature comprised between 5 and 20° C.

7. The method according to claim 6, wherein said cooling step is carried out at a temperature comprised between 15 and 20° C.

8. The method according to claim 1, wherein said at least one organic solvent is a polar aprotic organic solvent.

9. The method according to claim 1, wherein said at least one organic solvent is a ketone.

10. The method according to claim 9, wherein said ketone has from three to six carbon atoms.

11. The method according to claim 9, wherein said ketone is methylethylketone.

12. The method according to claim 1, wherein said fumaric acid is used in molar ratios comprised between 0.9:1.0 and 1.5:1.0 with respect to fesoterodine.

13. The method according to claim 12, wherein said fumaric acid is used in molar ratios comprised between 1.0:1.0 and 1.1:1.0 with respect to fesoterodine.

14. The method according to claim 1, wherein said fesoterodine is used in a g/l weight/volume ratio comprised between 3:1 and 10:1 with respect to said at least one organic solvent.

15. The method according to claim 1, wherein the fesoterodine fumarate thus obtained is filtered, washed, dried under vacuum and micronized.

16. The method according to claim 15, wherein the fesoterodine fumarate is micronized until obtaining a PSD with d (0.9)<20 micron.

17. The method of claim 1 wherein the fesoterodine fumarate obtained has a purity equal to 99.8% and less than 0.15% by mole of feso fumaric ester impurity.

* * * * *